United States Patent
Miller

[11] 3,975,532
[45] *Aug. 17, 1976

[54] HEXAHYDRO-1H-FURO(3,4-C) PYRROLE COMPOUNDS FOR TREATING PAIN

[75] Inventor: Alfred D. Miller, Wilmington, Del.

[73] Assignee: ICI United States Inc., Wilmington, Del.

[*] Notice: The portion of the term of this patent subsequent to Oct. 7, 1992, has been disclaimed.

[22] Filed: Apr. 9, 1975

[21] Appl. No.: 566,418

Related U.S. Application Data

[62] Division of Ser. No. 370,010, June 14, 1973, Pat. No. 3,910,950.

[52] U.S. Cl. .................................. 424/274
[51] Int. Cl.² ................................. A61K 31/40
[58] Field of Search ........................ 424/274

[56] References Cited
OTHER PUBLICATIONS

Chem. Abst. 71 – 124295k, (1969).
Chem. Abst. 67 – 32526a, (1967).
Chem. Abst. 67 – 100078h, (1967).
Chem. Abst. 76 – 25198c, (1972).
Chem. Abst. 77 – 151368s, (1972).
Chem. Abst. 78 – 71802j, (1973).
Chem. Abst. 79 – 5203j, (1973).
Achini et al., Tetrahedron Letters, No. 6, pp. 369–372, 2–75.
Toda et al., Bull. Chem. Soc. Jap., 47(2): 348–349, (1974).
Wooler et al., J. Org. Chem. 35(4), 888–898, (1970).
Achini et al., Tetrahedron Letters, No. 6, pp. 369–372, (1975).
Novitskii et al., Khim. Geterots Soed.(3): 406–410, (1969).

*Primary Examiner*—Stanley J. Friedman

[57] ABSTRACT

Disclosed are compounds, having the following general formula, which are useful as analgesics and/or anti-inflammatory agents in living animals (a)

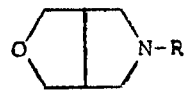

wherein R is a radical selected from the group consisting of hydrogen, aryl, alkenyl, aralkyl, halogen-substituted aralkyl, hydroxyl-substituted alkyl, arylsulfonyl, alicyclic, aroyl, alkylene dicarbonyl hexahydro-1H-furo (3,4-c)pyrrole, alkanoyl, arylene dicarbonyl hexahydro-1H-furo(3,4-c)pyrrole, halogen-substituted aroyl, arylethanoyl, halogen-substituted arylalkanoyl, halogen-substituted phenoxyalkanoyl, heteroaroyl, haloalkyl-substituted aroyl, alkyl-substituted aroyl, monoalkoxy-substituted aroyl, arylalkenoyl, hexahydrobenzoyl, alkanoyloxy-substituted aroyl, hydroxyl-substituted aroyl, and the pharmacologically acceptable acid addition salts thereof.

14 Claims, 1 Drawing Figure

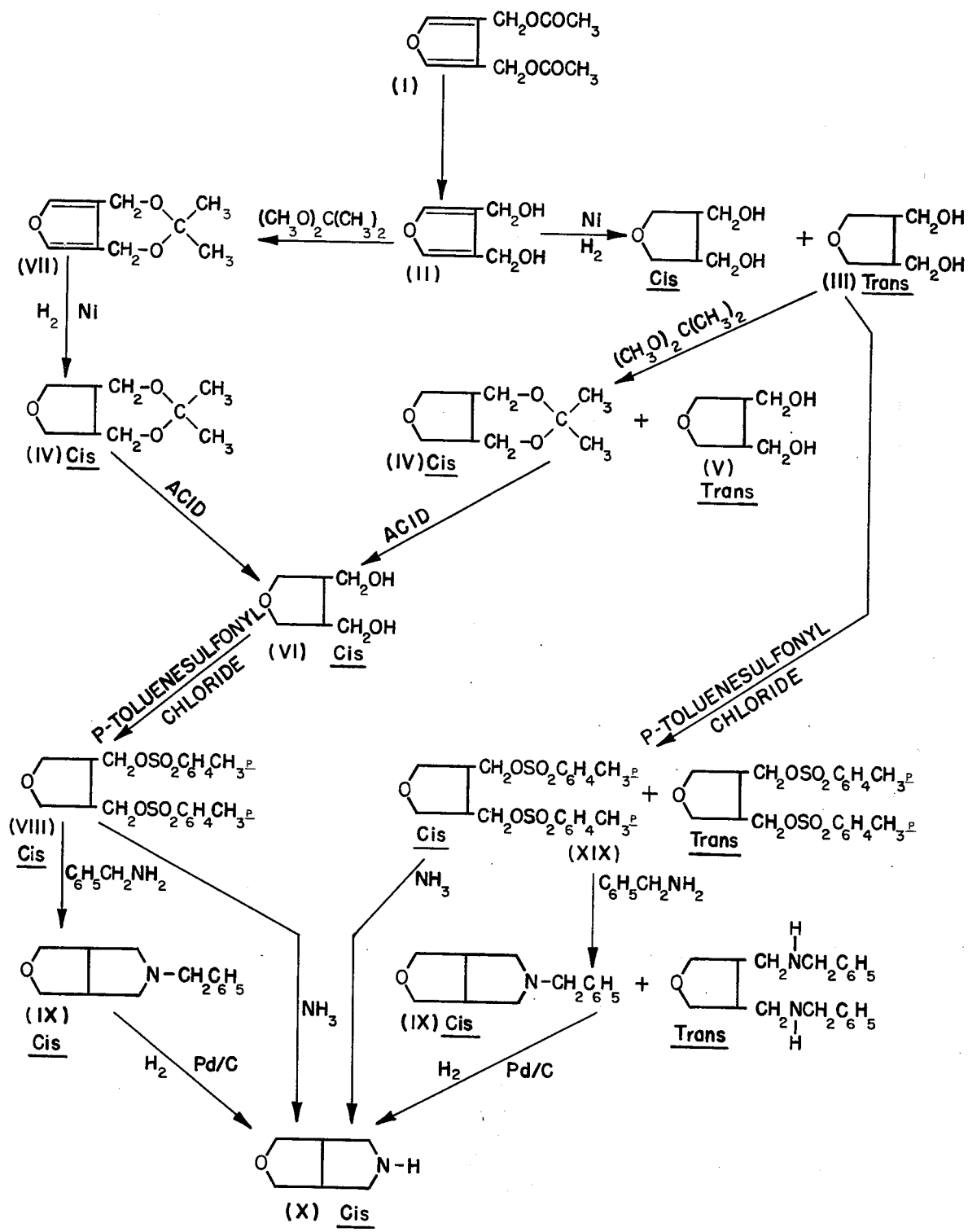

HEXAHYDRO-1H-FURO(3,4-c) PYRROLE COMPOUNDS FOR TREATING PAIN

This is a division of application Ser. No. 370,010, filed June 14, 1973, now U.S. Pat. No. 3,910,950.

This invention relates to hexahydro-1H-furo(3,4-c) pyrrole compounds and to their methods of preparation and use.

The physiologically active compounds of the present invention are illustrated by the following general formula (a) 

wherein R is a radical selected from the group consisting of hydrogen, aryl, alkenyl, aralkyl, halogen-substituted aralkyl, hydroxyl-substituted alkyl, arylsulfonyl, alicyclic, aroyl, alkylene dicarbonyl hexahydro-1H-furo(3,4-c)pyrrole, alkanoyl, arylene dicarbonyl hexahydro-1H-furo(3,4-c)pyrrole, halogen-substituted aroyl, arylethanoyl, halogen-substituted arylalkanoyl, halogen-substituted phenoxyalkanoyl, heteroaroyl, haloalkyl-substituted aroyl, alkyl-substituted aroyl, monoalkoxy-substituted aroyl, arylalkenoyl, hexahydrobenzoyl, alkanoyloxy-substituted aroyl, hydroxyl-substituted aroyl, and the pharmacologically acceptable acid addition salts thereof.

For purposes of exemplification and not limitation, the above radicals designated R in relation to formula (a) include the following within their scope. The term "aryl" as used herein by itself or in combination with other radicals is used to denote radicals, such as phenyl and naphthyl. By "alkenyl" is intended, for example, straight and branched chain radicals containing from 2 to 10 carbon atoms. The term "aralkyl" includes, for example, benzyl, phenethyl, methylbenzyl, 3-naphthylethyl, and 3-phenpropyl, wherein the alkyl portion of said radical contains from 1 to 10 carbon atoms. When halogen is referred to in relation to any of the radicals represented by R, all halogens are intended, and thus, fluorine, chlorine, iodine, and bromine are included; however, fluorine, chlorine and bromine are preferred. The term hydroxyl-substituted alkyl used herein is to denote alkyl radicals having from 1 to 10 carbon atoms substituted with at least 1, and no more than 6, hydroxyl groups. The radical arylsulfonyl includes, for example, benzenesulfonyl and naphthalenesulfonyl. For example, alicyclic includes cycloalkyl radicals having from 3 to 8 ring carbon atoms, such as, cyclopropyl, cyclopentyl, cyclohexyl, and cycloheptyl. Aroyl, as used herein by itself or in combination with other radicals, includes unsubstituted radicals, for example, naphthoyl and benzoyl. Alkanoyl as used herein in combination with other radicals includes such radicals having from 2 to 10 carbon atoms, for example, isobutyroyl, propionyl, acetyl, and caproyl. Therefore, the term arylalkanoyl includes radicals such as, for example, phenylacetyl, phenylcaproyl and naphthylpropionyl. When used by itself the term alkanoyl is used herein to define such radicals containing from 2 to 18 carbon atoms. The radical heteroaroyl includes, for example, nicotinoyl and thenoyl. When the term alkyl is used herein in combination with another radical to represent R above, it denotes straight and branch chain alkyl radicals containing from 1 to 10 carbon atoms.

For example, the alkyl portion of an alkyl-substituted aroyl radical will contain from 1 to 10 carbon atoms and the aroyl radical will be substituted with at least 1 and no more than 5 such alkyl groups, preferably 1 to 3 such alkyl groups. Haloalkyl-substituted aroyl radicals include aroyl radicals substituted with at least 1 and no more than 3 haloalkyl radicals each of which contains from 1 to 10 carbon atoms and at least 1 and no more than 6 halogen atoms. The alkoxy portion of the monoalkoxy substituted benzoyl radical contains from 1 to 10 carbon atoms and includes, for example, methoxybenzoyl and pentoxybenzoyl. The term arylalkenoyl as used herein includes radicals, such as cinnamoyl and other such radicals, wherein the alkenoyl portion of the radical contains from 2 to 10 carbon atoms. The term alkanoyloxy-substituted aroyl, as used herein, includes radicals, such as acetoxybenzoyl and acetoxynaphthoyl, wherein the alkanoyloxy portion of the radicals contains from 2 to 10 carbon atoms and the aroyl radical is substituted with at least 1 and no more than 3 alkanoyloxy radicals. Hydroxyl-substituted aroyl is used herein to denote aroyl radicals which are substituted with at least 1 and no more than 3 hydroxyl groups. The terms halogen-substituted aralkyl, halogen-substituted aroyl, halogen-substituted arylalkanoyl, and halogen-substituted phenoxyalkanoyl are used to indicate such radicals which are substituted with at least 1 and no more than 5 halogen atoms, preferably 1 to 3 halogen atoms.

In a preferred subclass of the present invention, R in formula (a) above is selected from the group consisting of: hydrogen; alkylene ($C_1$ to $C_8$) dicarbonyl hexahydro-1H-furo(3,4-c) pyrrole; phenylene dicarbonyl hexahydro-1H-furo(3,4-c)pyrrole; phenyl; phenylacetyl; monoalkoxy ($C_1$ to $C_4$) substituted benzoyl; phenylalkyl where the alkyl constituent thereof contains from 1 to 4 carbon atoms such as phenylpropyl, benzyl, and phenethyl; alkenyl ($C_3$ and $C_4$); mono-, di-, or tri-halogen substituted phenylalkyl where the alkyl group contains from 1 to 4 carbon atoms and the halogen is substituted on the phenyl ring; benzoyl; mono-, di-, or tri-halogen substituted benzoyl; mono-, di-, or tri-alkyl ($C_1$ to $C_4$) substituted benzoyl; mono-, di-, or tri-halogen substituted phenylalkanoyl wherein the alkanoyl group contains from 1 to 4 carbon atoms and the halogen is on the phenyl ring; hexahydrobenzoyl; phenylalkenoyl wherein the alkenoyl group is a lower alkenoyl containing from 3 to 5 carbon atoms, phenylethanoyl; halogen substituted phenoxyalkanoyl wherein the alkanoyl group contains from 1 to 4 carbon atoms and the phenoxy ring is substituted with from 1 to 3 halogen atoms; alkanoyl ($C_3$ to $C_{18}$); haloalkyl ($C_1$ to $C_4$) mono-, di-, or tri-substituted benzoyl wherein the haloalkyl group contains from 1 to 5 halogen atoms; mono- or di-hydroxyl substituted alkyl where the alkyl group contains from 1 to 4 carbon atoms; phenylsulfonyl; mono- or di-hydroxyl substituted benzoyl; nicotinoyl; mono- or di-alkanoyloxy ($C_1$ to $C_4$) substituted benzoyl; thenoyl; and cycloalkyl ($C_4$ to $C_8$). When halogen is referred to in this subclass, all halogens are intended; however, fluorine, chlorine, and bromine are preferred. In this preferred subclass, the above radicals, representing R in formula (a) above, can be substituted suitably in any of the ortho, meta, or para positions on the ring or any combination thereof unless otherwise directly indicated. For example, ring structures of the present preffered species of substituent R in formula (a) may be substituted in two ortho positions or two meta positions and/or the para position, or one ortho and one para position or any desired position combinations thereof.

The terms lower alkyl, lower alkoxy, lower haloalkyl, lower alkanoyl, and lower alkanoyloxy can be used to describe such radicals as referred to above in the preceding paragraph when they contain up to four carbon atoms.

Pharmacological studies indicate that the hexahydro-1H-furo(3,4-c)pyrrole compounds of the present invention are effective in alleviating pain in living animal bodies, more especially mammalian bodies. In general, the present compounds exhibit analgesic and/or anti-inflammatory activity. Test results in laboratory animals indicate that all of the subject compounds have analgesic activity except where R in formula (a) above is benzyl, hexahydrobenzoyl, o-acetoxybenzoyl, or phenylene dicarbonyl hexahydro-1H-furo(3,4-c)pyrrole and these compounds exhibit anti-inflammatory activity. As indicated, many of the present compounds exhibit analgesic/anti-inflammatory activity; and in addition, some of the present compounds also exhibit antipyretic activity.

In a further preferred subclass of the present invention, R in formula (a) above is selected from the group consisting of phenethyl, chlorophenethyl, hydrogen, cyclohexyl, benzoyl, benzyl, chlorobenzoyl, phenylacetyl, chlorophenylacetyl, chlorophenoxyacetyl, propionyl, nicotinoyl, trifluoromethylbenzoyl, dimethylbenzoyl, thenoyl, trimethylbenzoyl, propenyl, hydroxyethyl, benzenesulfonyl, hydroxybenzoyl, cinnamoyl, napthoyl, and the pharmacologically acceptable acid addition salts thereof.

In another preferred subclass of the present invention, R in formula (a) above is selected from the group consisting of hydrogen, o-acetoxybenzoyl, 2,4,6-trimethylbenzoyl, 2,6-dimethylbenzoyl, o-hydroxybenzoyl, p-chlorophenethyl, benzyl, cyclohexyl, phenyl, benzoyl, 1-naphthoyl, p-chlorobenzoyl, m-chlorobenzoyl, o-chlorobenzoyl, m-trifluoromethylbenzoyl, cinnamoyl, o-chlorophenylacetyl, m-chlorophenylacetyl, p-chlorophenylacetyl, hexahydrobenzoyl, propenyl, m-methoxybenzoyl, thenoyl, phenethyl, phenylacetyl, p-chlorophenoxyacetyl, propionyl, nicotinoyl, hydroxyethyl, benzenesulfonyl, and the pharmacologically acceptable acid addition salts thereof.

Among the novel compounds of the present invention are, for example: hexahydro-1H-furo(3,4-c)pyrrole hydrochloride; 5-phenylacetyl-hexahydro-1H-furo(3,4-c)pyrrole; 5-benzoyl-hexahydro-1H-furo(3,4-c)pyrrole; 5-(1-naphthoyl)-hexahydro-1H-furo (3,4-c)pyrrole; 5-(p-chlorobenzoyl)-hexahydro-1H-furo(3,4-c) pyrrole; 5-(m-chlorobenzoyl)-hexahydro-1H-furo(3,4-c)pyrrole; 5-(o-chlorobenzoyl)-hexahydro-1H-furo(3,4-c)pyrrole; 5-(m-trifluoromethylbenzoyl)-hexahydro-1H-furo(3,4-c)pyrrole; 5-cinnamoyl-hexahydro-1H-furo(3,4-c)pyrrole; 5-(o-chlorophenylacetyl)-hexahydro-1H-furo(3,4-c)pyrrole; 5-(m-chlorophenylacetyl)-hexahydro-1H-furo(3,4-c)pyrrole; 5-(p-chlorophenylacetyl)-hexahydro-1H-furo(3,4-c)pyrrole; 5-hexahydrobenzoyl-hexahydro-1H-furo(3,4-c)pyrrole; 5-propionyl-hexahydro-1H-furo(3,4-c)pyrrole; 5-(m-methoxybenzoyl)-hexahydro-1H-furo(3,4-c)pyrrole; 5-(2-thenoyl)-hexahydro-1H-furo(3,4-c)pyrrole; 5-nicotinoyl-hexahydro-1H-furo(3,4-c)pyrrole hydrochloride; 5-(p-chlorophenoxyacetyl)-hexahydro-1H-furo(3,4-c)pyrrole hydrochloride; 5-(o-acetoxybenzoyl)-hexahydro-1H-furo(3,4-c)pyrrole; 5-(2,4,6-trimethylbenzoyl)-hexahydro-1H-furo(3,4-c)pyrrole; 5-(2,6-dimethylbenzoyl)-hexahydro-1H-furo(3,4-c)pyrrole; 5-(o-hydroxybenzoyl)-hexahydro-1H-furo(3,4-c)pyrrole; 5,5'-adipyl-bis[hexahydro-1H-furo(3,4-c)pyrrole]; 5,5'-terephthaloyl-bis-[hexahydro-1H-furo(3,4-c)pyrrole]; 5-allyl-hexahydro-1H-furo(3,4-c)pyrrole acetate; 5-(2-hydroxyethyl)-hexahydro-1H-furo(3,4-c)pyrrole sulfate; 5-phenethyl-hexahydro-1H-furo(3,4-c)pyrrole hydrochloride; 5-(p-chlorophenethyl)-hexahydro-1H-furo(3,4-c)pyrrole hydrochloride; 5-benzyl-hexahydro-1H-furo(3,4-c)pyrrole hydrochloride; 5-cyclohexyl-hexahydro-1H-furo(3,4-c)pyrrole hydrochloride; 5-phenyl-hexahydro-1H-furo(3,4-c)pyrrole hydrochloride; 5-(benzenesulfonyl)-hexahydro-1H-furo(3,4-c)pyrrole; and the pharmacologically acceptable acid addition salts of such basic compounds.

The immediate precursor for making most of the novel compounds of the present invention is hexahydro-1H-furo(3,4-c) pyrrole. This compound, as shown in the accompanying schematic drawing, can be prepared by several different routes or processes. It will be noted in the following description and examples that the Roman numerals used to identify the various compounds are identical to and correspond to those used in the accompanying schematic drawing to identify like products.

Using 3,4-bis(acetoxymethyl)furan (I) as the starting material, 3,4-bis(hydroxymethyl)furan (II) can be suitably prepared via either a methanolysis or hydrolysis reaction process as illustrated in following Examples 1 and 2. The compound 3,4bis(acetoxymethyl)furan (I) can be purchased, for example, from the Aldrich Chemical Co., Inc., Milwaukee, Wisconsin, or prepared by methods described by H. Williams, P. Kaufmann and H. S. Mosher, Journal Organic Chemistry 20, 1139–1145, K. Alder and H. F. Rickett, Berichte der Deutschen Chemischen Gesellschaft 70, 1354 (1937), and E. C. Kornfeld and R. G. Jones, Journal Organic Chemistry 19, 1671–1680 (1954).

Using one of the optional routes of the present invention, 3,4-bis(hydroxymethyl)furan (II) can be hydrogenated to form a cis-trans mixture of 3,4-bis(hydroxymethyl)tetrahydrofuran (III) as shown in Example 3. This isomeric mixture (III) in turn can be separated by forming the isopropylidene ketal (IV) of the cis-isomer with 2,2-dimethoxypropane as illustrated in Example 4. If desired, suitable ketals other than the isopropylidene ketal can be prepared from the cis-isomer in order to obtain the desired separation. The trans-isomer does not form a ketal. Ketal (IV) can then by hydrolyzed in an acidic aqueous solution as shown in Example 5 to form cis 3,4-bis(hydroxymethyl) tetrahydrofuran (VI).

Alternatively, 3,4-bis(hydroxymethyl)furan (II) can be reacted with 2,2-dimethoxypropane in an acidic aqueous solution as shown in Example 6 to prepare the isopropylidene ketal (VII) of Compound (II). The ketal (VII) in turn can be hydrogenated as shown in Example 7 to form ketal (IV), which in turn can be hydrolyzed in an acidic-aqueous solution to cis 3,4-bis(hydroxymethyl) tetrahydrofuran (VI).

Continuing in the synthesis of the subject compounds, one mole cis-3,4-bis(hydroxymethyl)tetrahydrofuran (VI) is reacted with 2 moles of p-toluenesulfonyl chloride in pyridine to prepare cis 3,4-bis(tosyloxymethyl)tetrahydrofuran (VIII). This compound, (VIII), can in turn be reacted with an ammonia-alcohol solution under pressure as illustrated in Example 12 to form hexahydro-1H-furo(3,4-c)pyrrole (X). Alternatively, cis 3,4-bis(tosyloxymethyl)tetrahydrofuran (VIII) can be reacted with benzylamine as shown in Example 10 to form 5-benzyl-hexahydro-1H-furo(3,4-c)pyrrole (IX). This product, (IX), in turn can be debenzylated as shown in Example 11 to form hexahydro-1H-furo (3,4-c)pyrrole (X). All of the novel compounds of the present invention as well as those utilized in the claimed method of treatment are cis-isomers.

Using another route as shown in the accompanying schematic, one mole of the mixture of the cis-trans 3,4-bis (hydroxymethyl)tetrahydrofuran (III) can be reacted with p-toluenesulfonyl chloride according to the process of Example 9 to form a cis-trans mixture of 3,4-bis(tosyloxymethyl)tetrahydrofuran (XIX). This product, (XIX), can in turn be reacted with benzylamine according to the process of Example 10 to form 5-benzyl hexahydro-1H-furo(3,4-c)pyrrole (IX) from the cis 3,4-bis(tosyloxymethyl)tetrahydrofuran. 5-Benzyl hexahydro-1H-furo(3,4-c)pyrrole (IX) is separated from the reaction product mixture by distillation at about 95° to 105°C. at 0.15 mm Hg. This product in turn can be debenzylated according to the method of Example 11 to form hexahydro-1H-furo(3,4-c)pyrrole.

Alternatively, the cis-trans mixture of 3,4-bis(tosyloxymethyl)tetrahydrofuran (XIX) can be reacted with an ammonia-alcohol solution under pressure using the process of Example 12 to form hexahydro-1H-furo(3,4-c)pyrrole (X) which can be separated from the reaction mixture by distilling out at about 182°C. to 188°C.

While the above processes describe the reaction of 3,4-bis(tosyloxymethyl)tetrahydrofuran with amines, such as ammonia and benzylamine, to give hexahydro-1H-furo(3,4-c) pyrroles, it should be recognized by one skilled in the present art that the tosyloxy group can be replaced by other sulfonate-bearing groups (e.g., methanesulfonyloxy) and halogens (e.g., chlorine).

The various reactions and processes discussed above and disclosed in the accompanying drawing are more particularly described in following Examples 1 to 12.

EXAMPLE 1

Methanolysis of 3,4-Bis(Acetoxymethyl)Furan

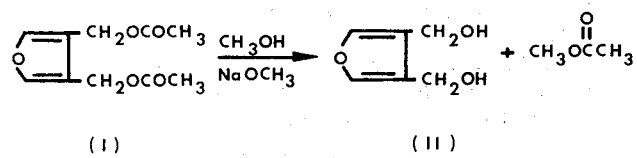

Methanol (2200 ml) was placed in a 5 liter, three-neck flask and 3 grams of sodium were added in small portions. The flask was equipped with a mechanical stirrer, an 8 inch Vigreaux column connected with a distillation head and condenser. After the sodium was completely dissolved, 1374 grams (6.48 moles) of 3,4-bis(acetoxymethyl)furan, represented by formula (I), were added. The reaction mixture was heated at 60°C. and the methyl acetate distilled as it was formed. Less than 2 hours were required to remove all the methyl acetate. Finally, the excess methanol was distilled and 3,4-bis(hydroxymethyl)furan, represented by formula (II), remained in the flask. Gas liquid chromatography was used to monitor the reaction and determine purity of the product.

EXAMPLE 2

Hydrolysis of 3,4-Bis(Acetoxymethyl)Furan

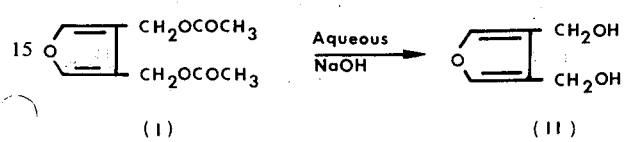

3,4-Bis(acetoxymethyl)furan, represented by formula (I), (1 kg, 4.71 moles) was placed in a three-neck flask equipped with a mechanical stirrer, thermometer, condenser, and dropping funnel. A solution of 500 grams (12.5 moles) of sodium hydroxide in 1500 ml water was added slowly through the dropping funnel. After one hour the reaction became exothermic and the temperature rose to 74°C. Hydrolysis was followed by gas liquid chromatographic analysis (Column 2' Carbowax 20M, temperature 190°C.). The reaction mixture was then cooled (ice water bath) to room temperature and the product was extracted with diethyl ether. After five extractions (1 pound diethyl ether each time), the reaction mixture was concentrated (until salts began to precipitate) and extracted in a continuous extractor. The gas liquid chromatography analysis indicated that the hydrolysis was quantitative.

EXAMPLE 3

Hydrogenation of 3,4-Bis(Hydroxymethyl) Furan - Preparation of cis and trans 3,4-Bis(Hydroxymethyl)Tetrahydrofuran

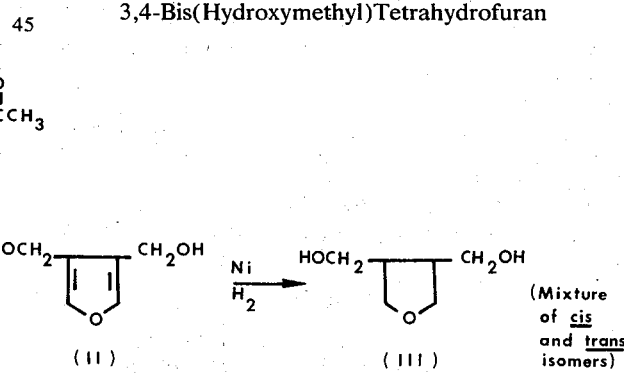

3,4-Bis(hydroxymethyl)furan, represented by formula (II), was hydrogenated to a mixture of cis and trans 3,4-bis (hydroxymethyl)tetrahydrofuran (III) (approximately 1:1) under the following conditions:

Temperature: 120°C.
Time: 3 hours
Pressure ($H_2$): 1150–1200 Psig
A typical charge:
Diol II = 800 grams Standard Ni (23%) = 160 grams
Ethanol = 1300 ml The completion of the reaction was determined by gas liquid chromatographic analysis (2' Carbowax 20M column at 235°C.). After completion of the reaction, the catalyst was filtered and the ethanol removed under reduced pressure.

EXAMPLE 4

Separation of cis-trans 3,4-Bis (Hydroxymethyl)Tetrahydrofuran — Formation of Isopropylidene Ketal of cis-3,4-Bis(Hydroxymethyl)Tetrahydrofuran

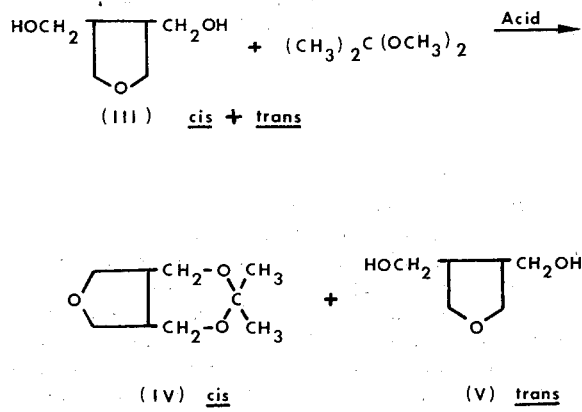

The separation of cis-trans isomers was accomplished by forming the isopropylidene ketal (IV) of the cis-isomer with 2,2-dimethoxypropane. The trans-isomer does not form a ketal. Ketal (IV) was separated from the trans-isomer by distillation.

1082 Grams (8.16 moles) of the diol, represented by formula (III), and 2,2-dimethoxypropane (1270 grams, 50% excess) were placed in a three-neck flask equipped with a thermometer, mechanical stirrer, and condenser and then 1.0 gram of p-toluenesulfonic acid monohydrate was added. As soon as the acid was added, the solution became clear and the temperature dropped to 16°C. The reaction mixture was stirred for 0.5 hour and then methanolic sodium hydroxide was added to the reaction mixture to make the reaction mixture slightly alkaline, that is, a pH of about 8 to 9. Completion of the reaction was determined by gas liquid chromatography.

After neutralization, the excess dimethoxypropane was stripped under reduced pressure and the ketal represented by formula (IV) distilled at 55° to 62°C./0.45 to 0.50 mm Hg. The trans 3,4-bis(hydroxymethyl)furan remained as pot residue or can be distilled.

EXAMPLE 5

Hydrolysis of Ketal (IV) — Isolation of cis 3,4-Bis(Hydroxymethyl)Tetrahydrofuran

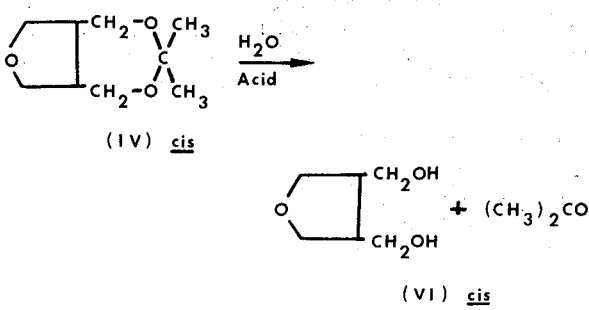

800 Grams (4.65 moles) of the ketal, represented by formula (IV), were hydrolyzed with 1.5 grams of p-toluenesulfonic acid monohydrate and 200 ml of H₂O. The reaction mixture was stirred for 0.5 to 1 hour at room temperature. The progress of the hydrolysis was followed by gas liquid chromatography. The reaction mixture was then neutralized with aqueous sodium hydroxide (2.0 grams/50 ml H₂O) to make the reaction mixture slightly alkaline, that is, a pH of about 8 to 9. After stripping water and dimethyl ketone, the cis diol (VI) was distilled under reduced pressure of 0.1 mm Hg at 120°C.

EXAMPLE 6

3,4-(Hydroxymethyl)Furan — Isopropylidene Ketal (VII)

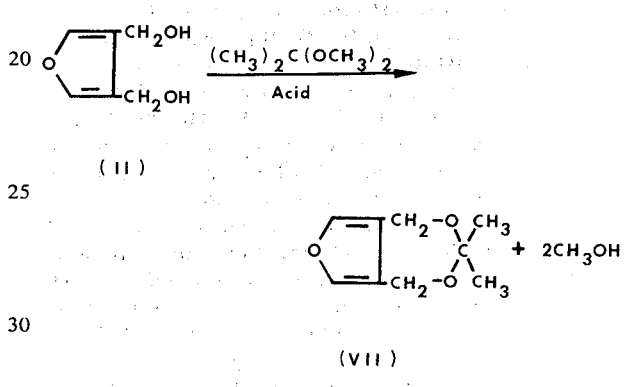

640 Grams (5 moles) of the diol, represented by formula (II), and 1560 grams (15 moles) of 2,2-dimethoxypropane were placed in a beaker and mixed with a magnetic stirrer. After the mixing, 2.0 grams of p-toluenesulfonic acid monohydrate were added. Instantly the reaction mixture became clear and the temperature dropped from 21° to 16°C. Gas liquid chromatographic analysis indicated completion of the reaction. Immediately, the methanol and the excess dimethoxypropane were removed in a vacuum rotary evaporator at a bath temperature of 40° to 45°C. and the ketal represented by formula (VII) was obtained.

The ketal, represented by formula (VII), is very unstable in solid state, and it is imperative to dissolve it in benzene immediately after the removal of methanol and the excess dimethoxypropane.

EXAMPLE 7

Hydrogenation of 3,4-Bis(Hydroxymethyl) Furan-Isopropylidene Ketal to cis-3,4-Bis(Hydroxymethyl)Tetrahydrofuran-Isopropylidene Ketal

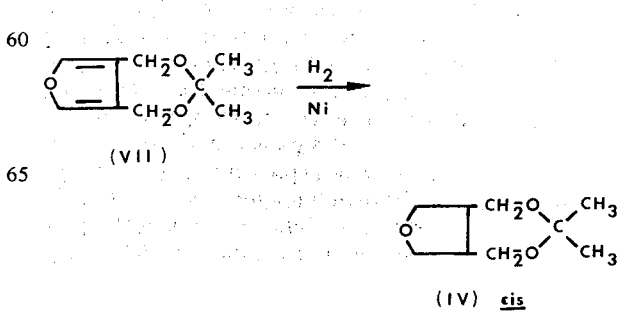

The ketal, represented by formula (VII) (from Example 6 — theoretically 860 grams) was dissolved in 700 ml benzene and placed in a gallon autoclave. Standard Ni catalyst (23% Ni) 225 grams in 300 ml benzene and 1 gram sodium methoxide were added and the ketal, represented by formula (VII) was hydrogenated at 125°C. and 1100 psig ($H_2$) for 4.5 hours. After completion of the hydrogenation, the catalyst was filtered and most of the benzene was distilled. Ketal (IV) was characterized by gas liquid chromatography and without further purification hydrolyzed to the cis diol, represented by formula (VI). Hydrolysis of the ketal, represented by formula (IV), to cis-3,4-bis(hydroxymethyl)-tetrahydrofuran is accomplished by the method of Example 5.

EXAMPLE 8 cis-3,4-Bis (Tosyloxymethyl) Tetrahydrofuran (VIII)

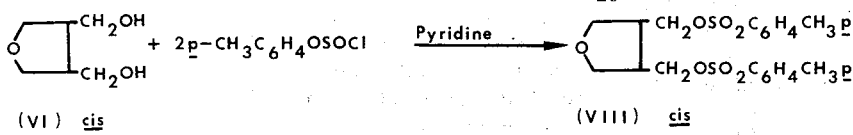

To a three-neck flask equipped with a thermometer, reflux condenser, mechanical stirrer, and dropping funnel were added 528.64 grams (4.0 moles) of the cis diol, represented by formula (VI), and 500 ml pyridine; and the mixture was cooled to 0° to 5°C. A solution of 1557 grams (8 moles) of p-toluenesulfonyl chloride in 1300 ml pyridine was added slowly through the dropping funnel. The temperature during the addition was kept below 10°C. After the addition of p-toluenesulfonyl chloride, the reaction mixture was stirred for 2 to 3 hours and then let stand at room temperature overnight.

The reaction mixture was poured over ice-water and stirred for 30 minutes; then the aqueous layer was decanted. The product was further purified by washing with distilled water.

EXAMPLE 9 cis-trans 3,4-Bis (Tosyloxymethyl) Tetrahydrofuran (XIX)

In a three-neck flask equipped with a thermometer, reflux condenser, mechanical stirrer, and dropping funnel were placed 323 grams (2.45 moles) of cis-trans 3,4-bis (hydroxymethyl) tetrahydrofuran, represented by formula (III), and 350 ml pyridine, and the mixture was cooled to 0° to 5°C. A solution of 953 grams (4.89 moles) p-toluenesulfonyl chloride (98%) in 700 ml of pyridine was added slowly through the dropping funnel. After the addition of p-toluenesulfonyl chloride, the reaction mixture was stirred for 2 to 3 hours and then let stand at room temperature overnight. The reaction mixture was poured over ice-water with rapid stirring. After stirring for 30 minutes, the product was a solid and the aqueous layer was decanted. The product cis-trans 3,4-bis(tosyloxymethyl)tetrahydrofuran represented by formulas (XIX), was washed many times with water and dried.

All of the compounds within the scope of the present invention, represented by formula (a) above, can be prepared in accordance with the principles and processes illustrated in the following Examples 10 to 43, with particular reference to types of reactions, types of reactants, ratios of reactants, reaction solvents, reaction times, temperatures, and other conditions cited. The compounds represented by formula (a) above where R is an acyl radical or substituted acyl radical are readily prepared by reacting hexahydro-1H-furo(3,4-c)pyrrole with an equal mole portion of an acyl chloride corresponding to the R substituent desired in a suitable solvent, such as an aqueous sodium hydroxide solution or benzene as illustrated in the following Examples 14 to 35 and 43. When substituent R of the compounds represented by formula (a) above is other than acyl, the subject compounds can be prepared by reacting the ditosylate compound represented by formulas (VIII) or (XIX) with an excess of an amine corresponding to the R substituent desired in a suitable solvent, such as triethylene glycol dimethyl ether as illustrated in Examples 36 to 42.

EXAMPLE 10

5-Benzyl-Hexahydro-1H-Furo(3,4-c)Pyrrole (IX)

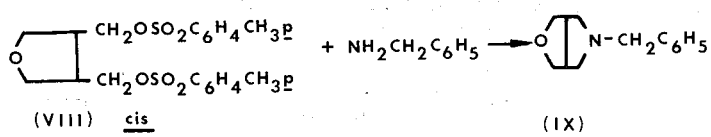

In a three-neck flask equipped with a mechanical stirrer, thermometer, and reflex condenser were placed 484.5 grams (1.1 moles) of the ditosylate, represented by formula (VIII), 353.6 grams (3.3 moles) of benzylamine and 500 ml of Ansul 141 (diethylene glycol dimethyl ether). The mixture was heated to 140°C., at which point the reaction became rather vigorous. The heating mantle was removed and the reaction mixture was cooled with cold water until the vigorous reaction subsided; then the reaction mixture was heated at 160°C. for 2.5 hours. The mixture was then cooled to 30° to 40°C. and a methanolic sodium hydroxide solution (88 grams NaOH in 400 ml $CH_3OH$) was added while stirring. Methanol (100 to 200 ml) should be added prior to the sodium hydroxide addition if the reaction mixture becomes too viscous when cooled to 30° to 40°C.

After stirring for 0.5 hour, the sodium tosylate was filtered and washed with ethyl ether/methanol (95:5). The filtrate and ether/methanol washings were combined and the organic solvents stripped under reduced pressure. During the stripping of solvents, additional salt precipitated and this was filtered and washed with ether/methanol. The solvents from the combined filtrates were stripped and product represented by formula (IX) distilled at 95° to 105°C./0.15 mm Hg.

The hydrochloride salt was formed by dissolving product (IX) in ether and passing in anhydrous HCl gas. The HCl salt of the product, represented by formula (IX), has a melting point of 182° to 183°C.

Analysis ($C_{13}H_{18}NOCl$). Calculated: C, 65.12%; H, 7.57%; N, 5.84%; Cl, 14.79%. Found: C, 65.12%; H, 7.55%; N, 5.86%, Cl, 14.74%.

EXAMPLE 11

Hexahydro-1H-Furo(3,4-c)Pyrrole (X) Prepared by Debenzylation of 5-Benzyl-Hexahydro-1H-Furo(3,4-c)Pyrrole

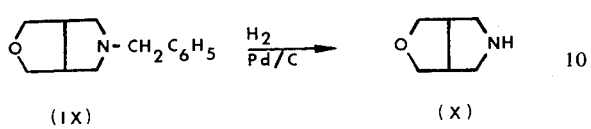

5-Benzyl-hexahydro-1H-furo(3,4-c)pyrrole, illustrated by formula (IX) (502 grams, 2.47 moles), 10% Palladium on carbon (30 grams), and 675 ml of absolute ethanol were placed in a 1-gallon autoclave. Hydrogen was added and the mixture was heated at 70°–75°C. for 4 hours at 70 psig. The reaction was monitored by the absorption of $H_2$ and gas liquid chromatographic analysis. The catalyst was filtered over Super Cel (diatomaceous earth) and the ethanol was stripped at atmospheric pressure. The product (X), a clear colorless liquid, distilled at 182° to 188°C.

Analysis ($C_6H_{11}NO$). Calculated: C, 63.66%; H, 9.82%; N, 12.37%. Found: C, 63.55%; H, 9.7%; N, 12.14%.

EXAMPLE 12

Reaction of cis-3,4-Bis(Tosyloxymethyl)Tetrahydrofuran and Ammonia

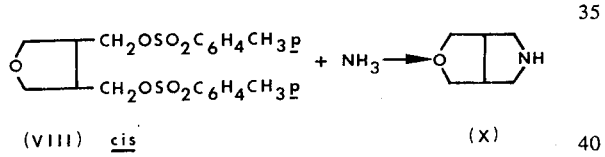

cis-3,4-Bis(tosyloxymethyl) tetrahydrofuran (190 grams), illustrated by formula (VIII), and liquid ammonia (100 grams) in a 1 liter of absolute ethanol were heated at 150°C. for 2 hours at 600 psig in a 1-gallon autoclave. The reaction mixture was cooled, treated with a methanolic sodium hydroxide solution (34.5 grams NaOH in 200 ml $CH_3OH$), filtered, and the solid washed with diethyl ether. The filtrate and ethereal washings were combined and the solvents were stripped at atmospheric pressure. Additional sodium-p-toluenesulfonate, which precipitated when most of the solvents were distilled, was removed by filtration, and the stripping was continued. The product (X) was distilled at atmospheric pressure at 182 to 188°C.

EXAMPLE 13

Hexahydro-1H-Furo(3,4-c)Pyrrole Hydrochloride

Hexahydro-1H-Furo(3,4-c)pyrrole (11.3 grams, 0.1 mole) was dissolved in 200 ml diethyl ether and anhydrous HCl gas passed through the solution. The salts were filtered and washed with ether.

Analysis ($C_6H_{12}NOCl$). Calculated: C, 48.16%; H, 8.09%; N, 9.36%; Cl, 23.70%. Found: C, 48.08%; H, 7.68%; N, 9.16%; Cl, 23.70%.

EXAMPLE 14

5-Phenylacetyl-Hexahydro-1H-Furo(3,4-c)Pyrrole

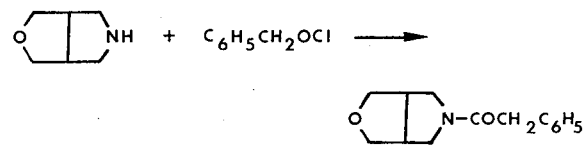

Phenylacetyl chloride (15.46 grams, 0.1 mole), Aldrich Chemical Co., Inc., Milwaukee, Wisconsin, was slowly added to a mixture of hexahydro-1H-furo(3,4-c)pyrrole hydrochloride (14.96 grams, 0.1 mole) and 300 ml aqueous sodium hydroxide (10.0 grams, 0.25 mole NaOH in water) at 10°C. After the phenylacetyl chloride addition, the ice bath was removed and the reaction mixture was stirred for 1.5 hours. The reaction mixture was extracted with diethyl ether (4 × 200 ml) and the extract treated with DARCO G-60 (activated carbon). Removal of diethyl ether gave 5-phenylacetyl-hexahydro-1H-furo(3,4-c)pyrrole (19.35 grams) a clear viscous liquid which solidified on cooling. This product was recrystallized from diethyl ether and had a melting point of 47.5° to 48.5°C.

Analysis for $C_{14}H_{17}NO_2$. Calculated: C, 72.70%; H, 7.41%; N, 6.06%. Found: C, 72.76%; H, 7.60%; N, 6.02%.

EXAMPLE 15

5-Benzoyl-Hexahydro-1H-Furo(3,4-c)Pyrrole

Benzoyl chloride (14.06 grams, 0.1 mole), Aldrich Chemical Co., Inc., Milwaukee, Wisconsin, was slowly added to a mixture of [compound (X)] hexahydro-1H-furo(3,4-c)pyrrole (11.3 grams, 0.1 mole) and sodium hydroxide (10 grams) in 300 ml of water at 10°C. After the addition of benzoyl chloride, the reaction mixture was stirred at room temperature for 2 to 3 hours and the product was extracted with diethyl ether (4 × 200 ml). Removal of the ether gave the product 5-benzoyl-hexahydro-1H-furo(3,4-c)pyrrole, represented by formula (XI), as a clear viscous liquid which solidified on standing. The product was crystallized from diethyl ether and had a melting point of 47° to 48°C.

Analysis for $C_{13}H_{15}NO_2$. Calculated: C, 71.90%; H, 6.92%; N, 6.46%. Found: C, 71.92%; H, 6.90%; N, 6.53%.

Using the procedure of Example 15, 0.1 mole portions of hexahydro-1H-furo(3,4-c)pyrrole [compound (X)] were reacted with 0.1 mole portions of other acyl chlorides listed in Table I below in aqueous sodium hydroxide solution to produce 5-acylhexahydro-1H-furo(3,4-c)pyrroles corresponding to the acyl radicals listed under the heading R in Table I.

TABLE I

5-Acyl-Hexahydro-1H-Furo(3,4-c)Pyrroles  

| Example Number | Acyl Chlorides | R | M.P. °C. | Found C | Found H | Found N | Found Cl, F or S | Calculated C | Calculated H | Calculated N | Calculated Cl, F or S |
|---|---|---|---|---|---|---|---|---|---|---|---|
| 16 | benzoyl chloride |  | 47–48 | 71.92 | 6.90 | 6.53 | — | 71.90 | 6.92 | 6.46 | — |
| 17 | 1-naphthoyl chloride (Eastman Kodak Co., Rochester, N.Y.) |  | 79–80.5 | 76.41 | 6.32 | 5.18 | — | 76.58 | 6.20 | 5.24 | — |
| 18 | p-chlorobenzoyl chloride (Aldrich Chemical Co., Inc., Milwaukee, Wis.) |  | Viscous Liquid | 62.04 | 5.42 | 5.53 | 14.19 | 62.03 | 5.61 | 5.57 | 14.09 (Cl) |
| 19 | m-chlorobenzoyl chloride (Aldrich Chemical Co., Inc.) |  | Viscous Liquid[1] | 61.89 | 5.59 | 5.46 | 14.01 | 62.03 | 5.61 | 5.57 | 14.09 (Cl) |
| 20 | o-chlorobenzoyl chloride (Aldrich Chemical Co., Inc.) |  | Viscous Liquid | 61.93 | 5.67 | 5.45 | 14.28 | 62.03 | 5.61 | 5.57 | 14.09 (Cl) |
| 21 | m-trifluoromethylbenzoyl chloride (Pierce Chemical Co., Rockford, Illinois) | 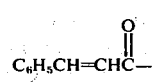 | Viscous Liquid[1] | 58.88 | 4.91 | 5.17 | 20.17 (F) | 58.94 | 4.95 | 4.91 | 19.88 (F) |
| 22 | cinnamoyl chloride (Aldrich Chemical Co., Inc.) | $C_6H_5CH{=}CHC-$ with =O | 130.5–131 | 74.10 | 7.17 | 5.72 | — | 74.04 | 7.04 | 5.76 | — |
| 23 | o-chlorophenylacetyl chloride | 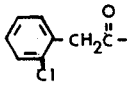 | 84.5–85 | 63.54 | 6.13 | 5.31 | 13.51 | 63.27 | 6.07 | 5.27 | 13.34 (Cl) |
| 24 | m-chlorophenylacetyl chloride | 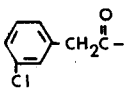 | 85.5–86.5 | 63.30 | 5.87 | 5.37 | 13.43 | 63.27 | 6.07 | 5.27 | 13.34 |
| 25 | p-chlorophenylacetyl chloride | 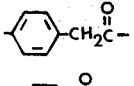 | 99.5–100 | 63.16 | 6.27 | 5.25 | 13.46 | 63.27 | 6.07 | 5.27 | 13.34 |
| 26 | hexahydrobenzoyl chloride (K&K Laboratories, Plainview, N.Y.) |  | 48.5–49.5 | 69.83 | 9.52 | 6.21 | — | 69.92 | 9.48 | 6.27 | — |
| 27 | propionyl chloride (Aldrich Chemical Co., Inc.) | $C_2H_5C-$ with =O | B.P.118°/ 0.05 mm Hg[2] | 64.22 | 8.67 | 8.39 | — | 63.88 | 8.93 | 8.27 | — |
| 28 | m-methoxybenzoyl chloride |  | Viscous Liquid[3] | 68.14 | 6.96 | 5.70 | — | 67.99 | 6.93 | 5.66 | — |
| 29 | 2-thenoyl chloride (J.T. Baker Chemical Co., Phillipsburg, N.J.) | 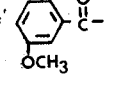 | 170–171 | 59.10 | 5.80 | 6.16 | 14.26 (S) | 59.17 | 5.87 | 6.27 | 14.36 (S) |

[1]Product was purified by column chromatography (silica gel-ether).
[2]Product was distilled.
[3]Product was distilled at 204–210°C. bath temperature at 0.150 mm Hg and purified by column chromatography (silica gel-ether).

EXAMPLE 30

5-Nicotinoyl-Hexahydro-1H-Furo(3,4-c)Pyrrole

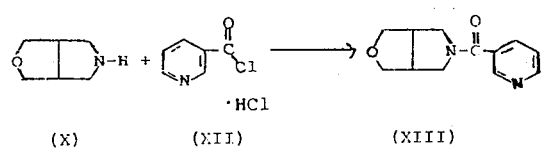

Nicotinoyl chloride hydrochloride, represented by formula (XII), (0.1 mole, 17.81 grams) was slowly added to a mixture of hexahydro-1H-furo(3,4-c)pyrrole, represented by formula (X), (0.1 mole, 11.3 grams), and triethylamine (0.2 mole, 20.24 grams) in 160 ml of benzene at 15°C. The reaction mixture was stirred for 1.5 hours at 15°C. and then left overnight at room temperature. The HCl salt of triethylamine was filtered and the salt was washed with benzene. The washings were combined with the filtrate and benzene was stripped under vacuum. The product, 5-nicotinoyl-hexahydro-1H-furo(3,4-c)pyrrole, represented by formula (XIII), light yellow viscous liquid, was purified by column chromatography (Alumina-eluted with methyl acetate).

Analysis for $C_{12}H_{14}O_2N_2$. Calculated: C, 66.03%; H, 6.46%; N, 12.83%. Found: C, 65.83%; H, 6.40%; N, 12.85%.

EXAMPLE 31

5-(p-Chlorophenoxyacetyl)-Hexahydro-1H-Furo(3,4-c)Pyrrole

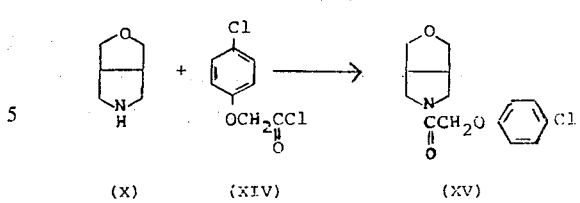

p-Chlorophenoxyacetyl chloride, represented by formula (XIV), (0.0813 mole, 16.65 grams) was slowly added to a mixture of hexahydro-1H-furo(3,4-c)pyrrole, represented by formula (X), (0.0813 mole, 9.20 grams), and triethylamine (0.0813 mole, 8.23 grams) in 160 ml benzene at 10°C. The reaction mixture was stirred for 18 hours while warming to room temperature.

The triethylamine hydrochloride salt that formed during the reaction was filtered and washed with benzene. The benzene wash and filtrate were combined and stripped of benzene via a rotary evaporator which effected crystallization. Recrystallization of the product from absolute ethanol, filtration and drying yielded fine white crystals of 5-(p-chlorophenoxyacetyl)hexahydro-1H-furo(3,4-c)pyrrole having a melting point of 109.5° to 110°C.

Analysis for $C_{14}H_{16}O_3NCl$. Calculated: C, 59.68%; H, 5.73%; N, 4.97%; Cl, 12.59%. Found: C, 59.51%; H, 5.79%; N, 4.94%; Cl, 12.79%.

Using the procedure of Examples 30 and 31, 0.1 mole portions of hexahydro-1H-furo(3,4-c)pyrrole were reacted with 0.1 mole portions of the acyl chlorides, listed in Table II below, in benzene and triethylamine (0.1 mole) as a base to produce the 5-acyl-hexahydro-1H-furo(3,4-c)pyrroles corresponding to the acyl radicals listed under the heading R in Table II.

TABLE II

5-Acyl-Hexahydro-1H-Furo(3,4-c)Pyrroles

| Example Number | Acyl Chlorides | R | M.P. or B.P. | Found C | Found H | Found N | Found Cl | Calculated C | Calculated H | Calculated N | Calculated Cl |
|---|---|---|---|---|---|---|---|---|---|---|---|
| 32 | o-acetoxybenzoyl chloride |  | B.P. 177–178° C./0.02 mm Hg | 65.31 | 6.18 | 5.12 | — | 65.44 | 6.23 | 5.04 | — |
| 33 | 2,4,6-trimethylbenzoyl chloride | 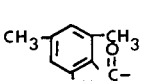 | Viscous Colorless Liquid | 74.17 | 8.07 | 5.31 | — | 74.10 | 8.16 | 5.40 | — |
| 34 | 2,6-dimethylbenzoyl chloride | 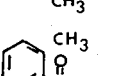 | Faint Yellow Viscous Liquid | 73.35 | 7.81 | 5.69 | — | 73.44 | 7.81 | 5.71 | — |
| 35 | o-hydroxybenzoyl chloride |  | M.P. 92–92.5°C. | 66.84 | 6.28 | 6.10 | — | 66.93 | 6.48 | 6.01 | — |
| 35" | 3,4-dichlorobenzoyl chloride | 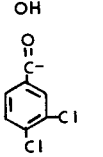 | Viscous Clear Liquid | 54.53 | 4.87 | 4.82 | 24.75 | 54.57 | 4.58 | 4.90 | 24.78 |

EXAMPLE 36

5-Allyl-Hexahydro-1H-Furo(3,4-c)Pyrrole

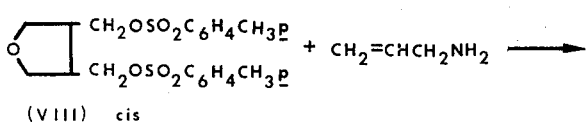

Allylamine (0.6 mole, 35 grams) and the ditosylate, represented by formula (VIII), (0.2 mole, 88.0 grams) in 300 ml of absolute ethanol were heated for 2 hours in an autoclave at 150°C. and 200 to 210 psig pressure. The reaction mixture was cooled and treated with ethanolic sodium hydroxide solution (13 grams NaOH). The sodium tosylate was filtered and the excess allylamine and ethanol were stripped from the filtrate at atmospheric pressure. The product 5-allyl-hexahydro-1-H-furo (3,4-c)pyrrole distilled as a colorless liquid at 56°C./0.5 mm of mercury pressure.

Analysis ($C_9H_{15}ON$). Calculted: C, 70.50%; H, 9.86%; N, 9.13%. Found: C, 70.47%; H, 9.71%; N, 8.99%.

EXAMPLE 37

5-(2-Hydroxyethyl)-Hexahydro-1-H-Furo(3,4-c)Pyrrole

Aminoethanol (0.8 mole, 48.9 grams) was reacted with cis-trans 3,4-bis(tosyloxymethyl)tetrahydrofuran, represented by formulas (XIX), (0.2 mole, 88.1 grams) in 150 ml of triethylene glycol dimethyl ether at 180°C. for 3 hours. The reaction mixture was cooled to room temperature and neutralized with 150 ml of methanolic sodium hydroxide solution (16 grams NaOH). After the reaction mixture was concentrated under aspirator pressure, 300 ml of diethyl ether was added and the sodium tosylate was filtered. The product 5-(2-hydroxyethyl)-hexahydro-1H-furo(3,4-c)pyrrole was distilled at 137° to 141°C./6.0 to 6.9 mm Hg.

Analysis ($C_8H_{15}NO_2$). Calcualted: C, 61.12%; H, 9.62%; N, 8.91%. Found: C, 61.05%; H, 9.64%; N, 8.87%.

EXAMPLE 38

5-Phenethyl-Hexahydro-1H-Furo(3,4-c)Pyrrole Hydrochloride

Phenethylamine (0.15 mole, 18.2 grams) was reacted with a mixture of the cis and trans isomers of 3,4-bis(-tosyloxymethyl)tetrahydrofuran, represented by formulas (XIX), (0.05 mole, 22.0 grams) in 60 ml triethylene glycol dimethyl ether at 185°C. for 3 hours. The reaction mixture was cooled to room temperature and neutralized with 75 ml methanolic sodium hydroxide solution (0.10 mole, 4.0 grams). After the reaction mixture was concentrated under aspirator pressure, 150 ml diethyl ether was added and sodium tosylate (18.5 grams) was filtered. Vacuum distillation of the filtrate gave 5-phenethyl-hexahydro-1H-furo(3,4-c)pyrrole (6.9 grams, b.p. 111° to 112°C./0.12 mm Hg). 5-Phenethyl-hexahydro-1H-furo(3,4-c)pyrrole was dissolved in 700 ml anhydrous diethyl ether and anhydrous hydrogen chloride was bubbled through the solution. The resulting 5-phenethyl-hexahydro-1H-furo(3,4-c)pyrrole hydrochloride was filtered, washed with ether, and dried. The product obtained had a melting point of 176° to 177°C.

Analysis ($C_{14}H_{20}NOCl$). Calculated: C, 66.23%; H, 7.94%; N, 5.52%; Cl, 13.97%. Found: C, 66.38%; H, 8.04%; N, 5.43%; Cl, 13.84%.

Using the procedure of Example 38, 0.05 mole portions of the cis-trans ditosylate, represented by formulas (XIX), were reacted with 0.15 mole portions of amines listed in Table III below to produce various compounds of the present invention corresponding to the alicyclic, aralkyl, and aryl radicals listed under the heading R in Table III. Obviously, the same type compounds can also be prepared directly from the cis ditosylate compound (VIII).

TABLE III

5-Aralkyl, Aryl, and Alicyclic-Hexahydro-1H-Furo(3,4-c)Pyrrole Hydrochlorides

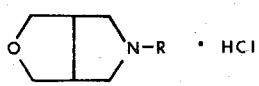

| Example Number | Amine Reactant | R | M.P. °C. HCl Salt | Found % C | H | N | Cl | Calculated % C | H | N | Cl |
|---|---|---|---|---|---|---|---|---|---|---|---|
| 39 | p-chlorophenethyl-amine | $pClC_6H_4CH_2CH_2$— | 174–175 | 58.52 | 6.57 | 4.76 | 24.50 | 58.34 | 6.64 | 4.86 | 24.61 |
| 40 | benzylamine | $C_6H_5CH_2$— | 182–183 | 65.12 | 7.55 | 5.86 | 14.74 | 65.12 | 7.57 | 5.84 | 14.79 |
| 41 | cyclohexylamine | (cyclohexyl)— | 247–249 | 62.32 | 9.80 | 6.05 | 15.49 | 62.18 | 9.57 | 6.04 | 15.30 |
| 42 | aniline | $C_6H_5$— | 152.5–158.5 | 63.87 | 7.27 | 6.22 | 15.78 | 63.85 | 7.15 | 6.21 | 15.71 |

EXAMPLE 43

5-(Benzenesulfonyl)-Hexahydro-1H-Furo(3,4-c)Pyrrole

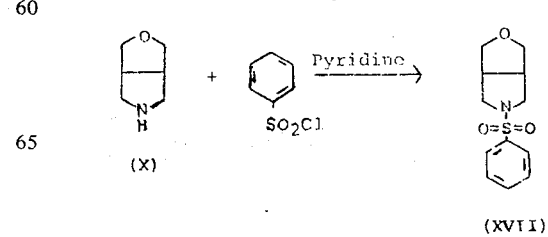

Benzenesulfonyl chloride (0.05 mole, 8.83 grams) dissolved in 15 ml pyridine was slowly added to a mixture of hexahydro-1H-furo(3,4-c)pyrrole, represented by formula (X), (0.05 mole, 5.66 grams) in 10 ml of pyridine at 5°C. The reaction mixture was stirred for 2 hours at 5°C. and then for 16 hours while warming to room temperature.

The reaction mixture was poured over an ice-water mixture which effected a precipitate. The crude product was filtered and washed with water to remove excess pyridine and pyridine hydrochloride. The product 5-(benzenesulfonyl)-hexahydro-1H-furo(3,4-c)pyrrole was recrystallized from methanol, obtaining upon filtration and drying, white crystals having a melting point of 104.5 to 105.5°C.

Analysis of ($C_{12}H_{15}O_3NS$). Calculated: C, 56.89%; H, 5.97%; N, 5.53%; S, 12.66%. Found: C, 57.04%; H, 5.91%; N, 5.56%; S, 12.76%.

EXAMPLE 44

5,5'-Terephthaloyl-Bis-[Hexahydro-1H-Furo(3,4-c)Pyrrole]

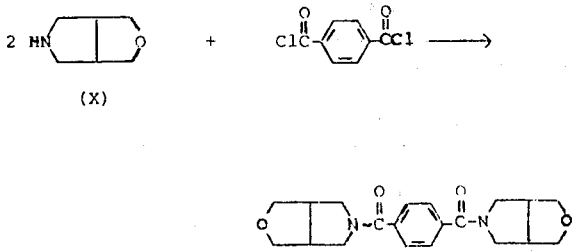

Terephthaloyl chloride (7.6 grams, 0.038 mole) was added to a mixture of hexahydro-1H-furo(3,4-c)pyrrole (8.5 grams, 0.075 mole), represented by formula (X) and triethylamine (7.6 grams, 0.075 mole) in 50 ml benzene at 6°C. The reaction mixture was stirred for 10 minutes and then allowed to warm at room temperature when the reaction became exothermic (temperature rose to 60°C.). The reaction mixture was then cooled and the triethylamine · hydrochloride was filtered. By adding ethyl ether to the filtrate (benzene), the product was precipitated as a white crystalline material. Finally, the product, 5,5'-terephthaloyl-bis-[hexahydro-1H-furo(3,4-c)pyrrole], was crystallized from benzene-ether (1:1) solution. The resulting dried product had a melting point of 191.5° to 193.0°C.

Analysis for $C_{20}H_{24}O_4N_2$. Calculated: C, 67.40%; H, 6.79%; N, 7.86%. Found: C, 67.83%; H, 6.84%; N, 7.78%.

EXAMPLE 45

5,5'-Adipyl-Bis-[Hexahydro-1H-Furo(3,4-c)Pyrrole]

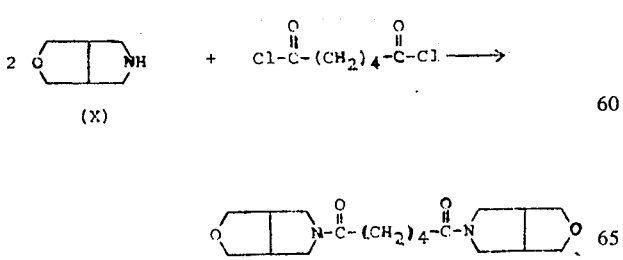

Adipyl chloride (12.81 grams, 0.07 mole) was added to a mixture of hexahydro-1H-furo(3,4-c)pyrrole (X) (15.84 grams, 0.14 mole) and triethylamine (14.20 grams, 0.14 mole) in 200 ml benzene at 10°C. The reaction mixture was stirred for 45 minutes at 10° to 15°C. and for 2 hours at room temperature. The triethylamine · hydrochloride was filtered and the filtrate was treated with Darco (G 60) activated carbon. By adding ethyl ether to the filtrate (benzene) the product was precipitated as a white crystalline material. Finally, the product, 5,5'-adipyl-bis-[hexahydro-1H-furo(3,4-c)pyrrole] was crystallized from benzene-ether (1:1) solution (m.p. 96 to 97.5°C.).

Analysis for $C_{18}H_{28}O_4N_2$. Calculated: C, 64.28%; H, 8.39%; N, 8.26%. Found: C, 64.15%; H, 8.12%; N, 8.11%.

EXAMPLE 46

5-Butyl-Hexahydro-1H-Furo(3,4-c)Pyrrole

Butylamine (0.416 mole, 30.4 grams) and the ditosylate, represented by formula (VIII) above, (0.14 mole, 61 grams) in 300 ml of absolute ethanol were heated for 2 hours in an autoclave at 150°C. and 200–210 psig pressure. The reaction mixture was cooled and treated with ethanolic sodium hydroxide solution (11.3 grams NaOH). The sodium tosylate was then filtered and the excess butylamine and ethanol were stripped at atmospheric pressure. The product, 5-butyl-hexahydro-1H-furo(3,4-c)pyrrole distilled as a colorless liquid at 81° to 85°C./3.5 mm of mercury pressure.

Analysis ($C_{10}H_{19}ON$). Calculated: C, 70.96%; H, 11.31%; N, 8.27%. Found: C, 71.08%; H, 11.13%; N, 8.28%.

Obviously, other 5-alkyl-hexahydro-1H-furo(3,4-c)pyrrole products can be prepared by the method of Example 45 by mere substitution of the alkylamine.

The physiologically or pharmacologically acceptable acid addition salts of the present pyrrole compounds are included within this invention. These acid addition salts are prepared by known processes, such as illustrated in several of the preceding examples, which involve reacting a free base compound of the present invention with an appropriate acid in a suitable solvent, for example, diethyl ether or ethyl alcohol. For example, among the mineral acids that can be used to prepare the subject acid addition salts are hydrochloric acid, hydrobromic acid, sulfuric acid, and phosphoric acid. Suitable organic acids that can be used to prepare the subject acid addition salts are, for example, acetic acid, methane-sulfonic acid, propionic acid, maleic acid, fumaric acid, tartaric acid, citric acid, and benzoic acid.

As shown in the above examples, the compounds of the present invention can be suitably purified by conventional methods, for example, by distillation, crystallization, or chromatography as indicated.

The acyl chloride reactants used to prepare the products of the present invention represented by formula (a) hereinabove where R is an acyl radical or substituted acyl radical can readily be prepared from their corresponding acid compound by reaction with an excess of a suitable agent, such as thionyl chloride, or phosphorus halides, such as $PCl_3$ and $PCl_5$. All of the acyl chloride reactants required for the preparation of the subject substituted compounds can be prepared by suitably using one of the well-known methods illustrated in Examples A to K. However, most of the acyl chlorides needed to prepare the subject compounds are commercially available.

EXAMPLE A p-Chlorophenoxyacetyl Chloride

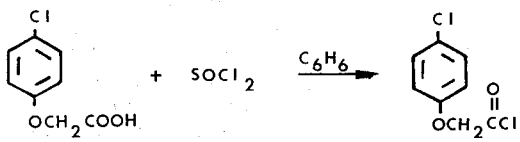

Thionyl chloride (0.431 mole, 51.26 grams) was slowly added to p-chlorophenoxyacetic acid (0.287 mole, 53.5 grams) in 160 ml of benzene at room temperature. The reaction mixture was refluxed for 18 hours. The excess thionyl chloride and benzene were stripped from reaction mixture under vacuum (aspirator) and the residue p-chlorophenoxyacetyl chloride was distilled at 70°C./0.05 mm Hg.

Using the procedure of Example A, a molar excess of thionyl chloride was reacted with portions of the acid compounds listed in Table IV to make the named acyl chloride products indicated. The molar ratio of thionyl chloride to acid reactant used, for example, can be within the range of 2:1 to 4:1. The exact amount of thionyl chloride used is not critical so long as it is in substantial molar excess in relation to the acid reactant. After the desired reaction is completed, the excess thionyl chloride is easily removed by stripping under vacuum. The boiling points of the various acyl chloride products prepared are listed next to these products in Table IV.

desired reaction is completed, the excess thionyl chloride is easily removed by stripping under vacuum.

EXAMPLE J

Salicylyl Chloride

A mixture of 10 grams salicylic acid, 7 ml of thionyl chloride, and 0.02 gram of aluminum chloride was heated at 40 to 45°C. for 1½ hours. The excess thionyl chloride was removed in vacuum and the salicylyl chloride reaction product can be used without further purification.

EXAMPLE K

Nicotinoyl Chloride-Hydrochloride

A mixture of 90 grams of nicotinic acid and 180 ml of thionyl chloride was heated at 55 to 65°C. for 3½ hours. The excess thionyl chloride was removed in vacuum and the nicotinoyl chloride-hydrochloride reaction product can be used without further purification.

Evaluation in laboratory animals indicates that the present compounds possess analgesic and/or anti-inflammatory activity when administered in a therapeutically effective amount. The effectiveness and dosage required vary, as is customary in this art, with the species being treated, particular disorder being treated, weight of the animal, and the route of administration. In accordance with the present invention, the subject compounds are administered at doses from about 0.5 milligram to 400 milligrams per kilogram body weight 1 to 4 times a day. A more preferred dose is from about 1.0 milligram to 300 milligrams per kilogram body weight 1 to 4 times a day.

TABLE IV

| Example | Acid Reactants | Acyl Chloride Products | Boiling Point |
|---|---|---|---|
| B | 2,4,6-trimethylbenzoic acid | 2,4,6-trimethylbenzoyl chloride | 48°C./0.05 mm Hg |
| C | m-methoxybenzoic acid | m-methoxybenzoyl chloride | 59°C./0.06 mm Hg |
| D | 2,6-dimethylbenzoic acid | 2,6-dimethylbenzoyl chloride | 38°C./0.05 mm Hg |
| E | o-acetoxybenzoic acid | o-acetoxybenzoyl chloride | 75.5–76°C./0.04 mm Hg |

EXAMPLE F m-Methoxybenzoyl Chloride

A mixture of 50 grams of m-methoxybenzoic acid and 125 ml of thionyl chloride was heated for 3 hours at 70°C. The excess thionyl chloride was stripped under vacuum to yield the desired acyl chloride product. The product 2-methoxybenzoyl chloride distilled at 77 to 78°C./1 to 2 mm Hg.

Using the procedure of Example F, a molar excess of thionyl chloride was reacted with portions of the acid compounds listed in Table V to make the acyl chloride products indicated. The molar ratio of thionyl chloride to acid reactant used, for example, can be within the range of 2:1 to 4:1. The exact amount of thionyl chloride used is not critical so long as it is in substantial molar excess in relation to the acid reactant. After the The analgesic and anti-inflammatory properties of the novel compounds of the present invention were determined by several different testing procedures. Among the tests used are, for example, the Rat Inflamed Paw Pressure Test, the Mouse Acetylcholine Writhing Test, and the Rat Carrageenan Edema Test, which can be carried out as follows:

Rat Inflamed Paw Pressure Test (Analgesic Test)

Non-fasted albino rats in the weight range of 160 to 180 grams are used. The experimental drugs are administered orally (10 ml/kg volume). Immediately after the administration, 0.1 ml of a 1% sodium carrageenan (Marine Colloids, Inc., Springfield, N.J.) in a sterile 0.9% aqueous solution of sodium chloride as injected into the subplantar region of the right hind paw. At a

TABLE V

| Example | Acid Reactants | Acyl Chloride Products | Boiling Point |
|---|---|---|---|
| G | o-chlorophenylacetic acid | o-chlorophenylacetyl chloride | — |
| H | m-chlorophenylacetic acid | m-chlorophenylacetyl chloride | — |
| I | p-chlorophenylacetic acid | p-chlorophenylacetyl chloride | 85°C./1.0 mm Hg | specific time post drug administration, the animal's right hand paw is placed between two plastic-grooved discs which are compressed by air pressure, and the amount of pressure required to induce vocalization and/or biting of the apparatus is recorded. The average pressure requirements for a drug-treated group of 6 animals is compared to that of a control group which receive 0.9% saline in place of the drug. The percent change of the test group from the control group is calculated.

5-Benzoyl-hexahydro-1H-furo(3,4-c)pyrrole when evaluated in this test had an $ED_{50}$ of 70 mg/kg body weight. Acetylsalicylic acid in the same test had an $ED_{50}$ of 1,500 mg/kg body weight, and codeine sulfate had an $ED_{50}$ of 167 mg/kg body weight. 5-(p-Chlorophenethyl)-hexahydro-1H-furo(3,4-c) pyrrole when evaluated in this test had an $ED_{50}$ of 72 mg/kg body weight.

Mouse Acetylcholine Writhing Test (Analgesic Test)

Female albino mice weighing 18 to 25 grams are administered the test drugs orally (10 ml/kg volume). One-half hour after administration of the test drug, acetylcholine bromide (11.0 ml/kg) is administered intraperitoneally (10 ml/kg) and the time to writhing recorded. The observation period extended for 10 minutes. Control animals dosed with 0.9% saline (10 ml/kg) are tested simultaneously. The percent inhibition of writhing is calculated from the number that did not writhe in 2 minutes post injection of the acetylcholine bromide.

5-Benzoyl-hexahydro-1H-furo(3,4-c)pyrrole when evaluated in this test had an $ED_{50}$ of 210 mg/kg body weight. Acetylsalicylic acid in the same test had an $ED_{50}$ of 150 mg/kg body weight and codeine sulfate had an $ED_{50}$ of 46 mg/kg body weight. 5-(p-Chlorophenethyl)-hexahydro-1H-furo(3,4-c)pyrrole when evaluated in this test had an $ED_{50}$ of 72 mg/kg body weight.

Rat Carrageenan Edema Test (Anti-inflammatory Test)

Non-fasted albino rats in the weight range of 160 to 180 grams are used. The test drugs are administered orally. Immediately following administration of the drug, 0.1 ml of a 1% carrageenan suspension (Marine Colloids, Inc., Springfield, N.J.) in a sterile 0.9% aqueous solution of sodium chloride is injected into the subplantar area of the right hind paw and the foot volume measured by volume displacement. The foot volume is measured again at 4 hours post injection of the drug and the percent change in volume when compared to a control group receiving 0.9% saline instead of the drug is calculated.

5-Benzoyl-hexahydro-1H-furo(3,4-c)pyrrole when evaluated in this test had an $ED_{50}$ of 690 mg/kg body weight. Acetylsalicylic acid in this test had an $ED_{50}$ of 110 mg/kg body weight. Codeine sulfate exhibited no activity in this test. 5-(p-Chlorophenethyl)-hexahydro-1H-furo(3,4-c)pyrrole when evaluated in this test had an $ED_{50}$ of 600 mg/kg body weight.

The compounds 5-hexahydrobenzoyl-hexahydro-1H-furo (3,4-c)pyrrole, 5-(o-acetoxybenzoyl)-hexahydro-1H-furo(3,4-c)pyrrole and 5-benzyl-hexahydro-1H-furo(3,4-c)pyrrole at 300 mg/kg body weight gave 20% inhibition against edema caused by the injection of sodium carrageenan under the conditions of this anti-inflammatory test.

The designation $ED_{50}$ is used hereinabove to designate a dose level which showed significant activity in 50% of the animals tested.

As the compounds within the scope of this invention are effective upon oral administration, they can be compounded into any suitable oral dosage form, such as in tablet, capsule, syrup, elixir, suspension or other solid or liquid forms that can be prepared by procedures well known in the art. Thus, the subject novel compounds can be mixed with a suitable diluent, such as lactose or kaolin, and encapsulated; or they can be combined with suitable binding agents and expanding agents and compressed into tablets. In addition, a liquid pharmaceutical may be obtained by dissolving, dispersing, or suspending novel compounds of this invention with a suitable flavored liquid. The present compounds are also considered active upon parenteral and rectal administration.

Examples of formulations for preparing tablets, capsules, liquids, parenterals, and suppositories containing the novel compounds of the present invention are described below. Obviously, it will be recognized by one skilled in the present art that the following formulations represent only one method of preparing such pharmaceutical compositions and obviously the size of the tablet or capsule or the strength of the dosage form may be suitably varied in order to satisfy the particular requirements, such as dosage level indicated. For example, each dosage unit may conveniently contain from about 15 milligrams to 5,000 milligrams of the active ingredient admixed with a diluent amount of a pharmaceutically acceptable carrier. Any of the well-known suitable pharmaceutical carriers can be used to prepare acceptable dosage forms so as to provide an effective amount of therapeutically effective amount of the compound to be administered.

| Tablet Containing 100 mg of 5-Cinnamoyl Hexahydro-1H-Furo(3,4-c)Pyrrole | 1000 Tablets (Grams) |
|---|---|
| 5-Cinnamoyl Hexahydro-1H-Furo(3,4-c)Pyrrole | 100 |
| Starch | 80 |
| Powdered Lactose | 80 |
| Talc | 20 |
| Weight of Granulation | 280 |

Combine all ingredients, mix, and then compress into slugs. The slugs should then be ground to form granules that will pass through a 14 to 16 mesh screen. The granules may then be recompressed into tablets using a suitable compression mold to form tablets, each weighing 280 mg.

Capsule Containing 200 mg. of
5-(m-Chlorophenylacetyl)Hexahydro-1H-Furo(3,4-c)Pyrrole

| 5-(m-Chlorophenylacetyl)Hexahydro-1H-Furo(3,4-c)Pyrrole | 200 mg |
|---|---|
| Powdered Lactose | 100 mg |
| D.T.D. Capsules No. 1000 | |

Mix the ingredients so as to evenly distribute the active ingredient throughout the lactose. Pack the powder into a No. 1 empty gelatin capsule.

Suspension Containing 50 mg per 5 cc of
5-Benzoyl-Hexahydro-1H-Furo(3,4-c)Pyrrole

| | |
|---|---|
| 5-Benzoyl-Hexahydro-1H-Furo(3,4-c)Pyrrole | 10 grams |
| Tragacanth | 50 grams |
| Amaranth | 10 grams |
| Syrup Wild Cherry | 60 ml |
| Distilled Water q.s. | 1000 ml |

Hydrate the tragacanth with sufficient water to form a smooth past and to this add the 5-benzoyl-hexahydro-1H-furo(3,4-c)pyrrole, followed by the amaranth which has been previously dissolved in water. Then add the syrup of wild cherry and add distilled water to make 1000 ml.

Injectable Containing 5 mg of
5-Nicontinoyl-Hexahydro-1H-Furo(3,4-c)Pyrrole Per Milliliter Suitable for Intramuscular, Intraperitoneal of Subcutaneous Injection

| | |
|---|---|
| 5-Nicotinoyl-Hexahydro-1H-Furo(3,4-c)Pyrrole | 5.0 grams |
| Chlorobutanol | 3.0 grams |
| Propylene Glycol | 20.0 ml |
| Water for Injection q.s. | 1000.0 ml |

Combine the above ingredients, clarify by filtration, fill into vials, seal, and autoclave.

Suppository Containing 200 mg of
5-Phenethyl-Hexahydro-1H-Furo(3,4-c)Pyrrole Hydrochloride

| | |
|---|---|
| 5-Phenethyl-Hexahydro-1H-Furo(3,4-c)Pyrrole | 0.2 gram |
| Cocoa Butter | 1.8 grams |
| Make of Such No. 100 | |

Melt cocoa butter and disperse the 5-phenethyl-hexahydro-1H-furo(3,4-c)pyrrole hydrochloride in the molten mass and stir until uniform. Pour the resulting molten mass into suppository mold and chill. Remove suppositories from mold and package.

Having thus described my invention, I claim:

1. A method of alleviating pain in a living animal comprising administering to said animal a therapeutically effective amount of a compound represented by the formula

wherein R is a radical selected from the group consisting of hydrogen; alkylene ($C_1$ to $C_8$) dicarbonyl hexahydro-1H-furo(3,4-c)pyrrole; phenylene dicarbonyl hexahydro-1H-furo(3,4-c)pyrrole; phenyl; phenylacetyl; monoalkoxy ($C_1$ to $C_4$) substituted benzoyl; phenylalkyl where the alkyl constituent thereof contains from 1 to 4 carbon atoms; alkenyl ($C_3$ and $C_4$); mono-, di-, or tri-halogen substituted phenylalkyl where the alkyl group contains from 1 to 4 carbon atoms and the halogen is substituted on the phenyl ring; benzoyl; mono-, di-, or tri-halogen substituted benzoyl; mono-, di-, or tri-alkyl ($C_1$ to $C_4$) substituted benzoyl; mono-, di-, or tri-halogen substituted phenylalkanoyl wherein the alkanoyl group contains from 2 to 4 carbon atoms and the halogen is on the phenyl ring; hexahydrobenzoyl; phenylalkenoyl wherein the alkenoyl group is a lower alkenoyl containing from 3 to 5 carbon atoms; phenylethanoyl; halogen-substituted phenoxyalkanoyl wherein the alkanoyl group contains from 1 to 4 carbon atoms and the phenoxy ring is substituted with from 1 to 3 halogen atoms; alkanoyl ($C_3$ to $C_{18}$); haloalkyl ($C_1$ to $C_4$) mono-, di-, or tri-substituted benzoyl wherein the haloalkyl group contains from 1 to 5 halogen atoms; mono- or di-hydroxyl substituted alkyl where the alkyl group contains from 1 to 4 carbon atoms; phenylsulfonyl; mono- or di-hydroxyl substituted benzoyl; nicotinoyl; mono- or di-alkanoyloxy ($C_1$ to $C_4$) substituted benzoyl; thenoyl; cycloakyl ($C_4$ to $C_8$); and a pharmacologically acceptable acid addition salt thereof.

2. A method of alleviating pain in a living animal comprising administering to said animal a therapeutically effective amount of a compound represented by the formula

wherein R is a radical selected from the group consisting of butylphenethyl, chlorophenethyl, hydrogen, cyclohexyl, benzoyl, benzyl, chlorobenzoyl, phenylacetyl, chlorophenylacetyl, chlorophenoxyacetyl, propionyl, nicotinoyl, trifluoromethylbenzoyl, dimethylbenzoyl, thenoyl, trimethylbenzoyl, propenyl, hydroxyethyl, benzenesulfonyl, hydroxybenzoyl, cinnamoyl, naphthoyl, and the pharmacologically acceptable acid addition salts thereof.

3. A method of alleviating pain in a living animal comprising administering to said animal a therapeutically effective amount of a compound represented by the formula

wherein R is a radical selected from the group consisting of hydrogen, o-acetoxybenzoyl, 2,4,6-trimethylbenzoyl, 2,6-dimethylbenzoyl, o-hydroxybenzoyl, p-chlorophenethyl, benzyl, cyclohexyl, phenyl, benzoyl, 1-naphthoyl, p-chlorobenzoyl, m-chlorobenzoyl, o-chlorobenzoyl, m-trifluoromethylbenzoyl, cinnamoyl, o-chlorophenylacetyl, m-chlorophenylacetyl, p-chlorophenylacetyl, hexahydrobenzoyl, propenyl, m-methoxybenzoyl, thenoyl, phenethyl, phenylacetyl, p-chlorophenoxyacetyl, propionyl, nicotinoyl, hydroxyethyl, benzenesulfonyl, and the pharmacologically acceptable acid addition salts thereof to an animal susceptible thereto.

4. A method of producing analgesia in a living animal comprising administering to said animal a therapeutically effective amount of a compound represented by the formula

wherein R is a radical selected from the group consisting of benzoyl, naphthoyl, phenacetyl, p-chlorobenzoyl, m-chlorobenzoyl, o-chlorobenzoyl, m-trifluoromethylbenzoyl, cinnamoyl, o-chlorophenylacetyl, m-chlorophenylacetyl, p-chlorophenylacetyl, p-chlorophenoxyacetyl, propinonyl, m-methoxybenzoyl, 2-thenoyl, 2,4,6-trimethylbenzoyl, 2,6-dimethylbenzoyl, 3-nicotinoyl, and o-hydroxybenzoyl, and the pharmacologically acceptable acid addition salts thereof.

5. A method of producing analgesia in a living animal comprising administering to said animal a therapeutically effective amount of 5-benzoyl-hexahydro-1H-furo(3,4-c)pyrrole.

6. A method of alleviating pain in a living animal comprising administering to said animal a therapeutically effective amount of an analgesic or anti-inflammatory agent represented by the formula

wherein R is a radical selected from the group consisting of hydrogen; alkylene ($C_1$ to $C_8$) dicarbonyl hexahydro-1H-furo(3,4-c)pyrrole; phenylene dicarbonyl hexahydro-1H-furo(3,4-c)pyrrole; phenyl; phenylacetyl; monoalkoxy ($C_1$ to $C_4$) substituted benzoyl; phenylalkyl where the alkyl constituent thereof contains from 1 to 4 carbon atoms; alkenyl ($C_3$ and $C_4$); mono-, di-, or tri-halogen substituted phenylalkyl where the alkyl group contains from 1 to 4 carbon atoms and the halogen is substituted on the phenyl ring; benzoyl; mono-, di-, or tri-halogen substituted benzoyl; mono-, di-, or tri-alkyl ($C_1$ to $C_4$) substituted; mono-, di-, or tri-halogen substituted phenylalkanoyl wherein the alkanoyl group contains from 2 to 4 carbon atoms and the halogen is on the phenyl ring; hexahydrobenzoyl; phenylalkenoyl wherein the alkenoyl group is a lower alkenoyl containing from 3 to 5 carbon atoms; phenylethanoyl; halogen-substituted phenoxyalkanoyl wherein the alkanoyl group contains from 1 to 4 carbon atoms and the phenoxy ring is substituted with from 1 to 3 halogen atoms; alkanoyl ($C_3$ to $C_{18}$); haloalkyl ($C_1$ to $C_4$) mono-, di-, or tri-substituted benzoyl wherein the haloalkyl group contains from 1 to 5 halogen atoms; mono- or di-hydroxyl substituted alkyl where the alkyl group contains from 1 to 4 carbon atoms; phenylsulfonyl; mono- or di-hydroxyl substituted benzoyl; nicotinoyl; mono- or di-alkanoyloxy ($C_1$ to $C_4$) substituted benzoyl; thenoyl; cycloalkyl ($C_4$ to $C_8$); and the pharmacologically acceptable acid addition salts thereof to an animal susceptible thereto.

7. A method of producing analgesia in a living animal comprising administering a therapeutically effective amount of 5-alkyl ($C_1$ to $C_4$)-hexahydro-1H-furo(3,4-c)pyrrole or a pharmacologically acceptable acid addition salt thereof to an animal.

8. A method of claim 7 wherein the compound is 5-butylhexahydro-1H-furo(3,4-c)pyrrole.

9. A composition for alleviating pain in a living animal comprising an effective amount of a compound represented by the formula

wherein R is a radical selected from the group consisting of butyl, phenethyl, chlorophenethyl, hydrogen, cyclohexyl, benzoyl, benzyl, chlorobenzoyl, phenylacetyl, chlorophenylacetyl, chlorophenoxyacetyl, propionyl, nicotinoyl, trifluoromethylbenzoyl, dimethylbenzoyl, thenoyl, trimethylbenzoyl, propenyl, hydroxyethyl, benzenesulfonyl, hydroxybenzoyl, cinnamoyl, naphthoyl, and the pharmacologically acceptable acid addition salts thereof in a pharmaceutical carrier.

10. A composition for alleviating pain in a living animal comprising an effective amount of a compound represented by the formula

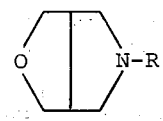

wherein R is a radical selected from the group consisting of hydrogen, o-acetoxybenzoyl, 2,4,6-trimethylbenzoyl, 2,6-dimethylbenzoyl, o-hydroxybenzoyl, p-chlorophenethyl, benzyl, cyclohexyl, phenyl, benzoyl, 1-naphthoyl, p-chlorobenzoyl, m-chlorobenzoyl, o-chlorobenzoyl, m-trifluoromethylbenzoyl, cinnamoyl, o-chlorophenylacetyl, m-chlorophenylacetyl, p-chlorophenylacetyl, hexahydrobenzoyl, propenyl, m-methoxybenzoyl, thenoyl, phenethyl, phenylacetyl, p-chlorophenoxyacetyl, propionyl, nicotinoyl, hydroxyethyl, benzenesulfonyl, and the pharmacologically acceptable acid addition salts thereof in a pharmaceutical carrier.

11. A composition for alleviating pain in a living animal comprising an effective amount of a compound represented by the formula

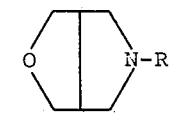

wherein R is a radical selected from the group consisting of benzoyl, naphthoyl, phenacetyl, p-chlorobenzoyl, m-chlorobenzoyl, o-chlorobenzoyl, m-trifluoromethylbenzoyl, cinnamoyl, o-chlorophenylacetyl, m-chlorophenylacetyl, p-chlorophenylacetyl, p-chlorophenoxyacetyl, propinonyl, m-methoxybenzoyl, 2-thenoyl, 2,4,6-trimethylbenzoyl, 2,6-dimethylbenzoyl, 3-nicotinoyl, and o-hydroxybenzoyl, and the pharmacologically acceptable acid addition salts thereof in a pharmaceutical carrier.

12. A composition of claim 9 wherein the compound is 5-benzoyl-hexahydro-1H-furo(3,4-c)pyrrole.

13. A composition for alleviating pain in a living animal comprising an effective amount of 5-alkyl ($C_1$ to $C_4$) hexahydro-1H-furo(3,4-c)pyrrole or a pharmacologically acceptable acid addition salt thereof in a pharmaceutical carrier.

14. A composition for alleviating pain in a living animal comprising an effective amount of 5-butyl-hexahydro-1H-furo(3,4-c)pyrrole in a pharmaceutical carrier.

* * * * *

UNITED STATES PATENT AND TRADEMARK OFFICE
CERTIFICATE OF CORRECTION

PATENT NO. : 3,975,532
DATED : August 17, 1976
INVENTOR(S) : Alfred D. Miller

It is certified that error appears in the above-identified patent and that said Letters Patent are hereby corrected as shown below:

Column 2, line 45, "1 to 4" should read -- 2 to 4 --.

Column 2, line 67, "preffered" should read -- preferred --.

Column 4, line 37, after "1139-1145" insert -- (1955) --.

Column 8, line 15, "3,4-(Hydroxymethyl)Furan" should read -- 3,4-Bis(Hydroxymethyl)Furan --.

Column 10, line 40, "reflex" should read -- reflux --.

Column 11, line 27, "9.7%" should read -- 9.78% --.

Column 13, Example 29, 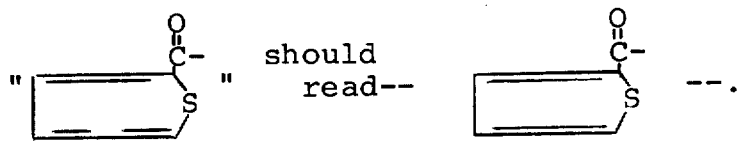

Column 15, Example 34, 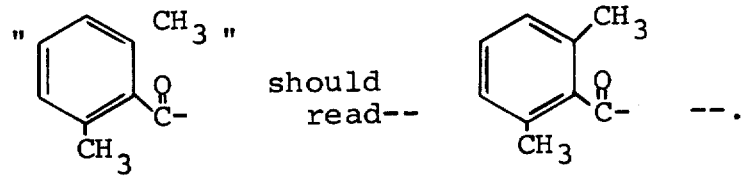

Column 17, Example 42, "158.5" should read -- 153.5 --.

Column 17, line 66, "Calcualted" should read -- calculated --.

Column 22, line 60, "as injected" should read -- is injected --.

Column 24, line 35, "amount of therapeutically" should read -- amount or therapeutically --.

UNITED STATES PATENT AND TRADEMARK OFFICE
CERTIFICATE OF CORRECTION

PATENT NO. : 3,975,532

DATED : August 17, 1976

INVENTOR(S) : Alfred D. Miller

Page 2 of 2

It is certified that error appears in the above-identified patent and that said Letters Patent are hereby corrected as shown below:

Column 25, line 11, "past" should read -- paste --.

Column 25, line 19, "of" should read -- or --.

Column 26, line 14, "cycloakyl" should read -- cycloalkyl --.

Column 27, line 45, after "substituted" and before "; mono-" insert -- benzoyl --.

Signed and Sealed this

Eighth Day of November 1977

[SEAL]

Attest:

RUTH C. MASON
Attesting Officer

LUTRELLE F. PARKER
Acting Commissioner of Patents and Trademarks